United States Patent [19]

Shaw et al.

[11] Patent Number: 4,964,957
[45] Date of Patent: Oct. 23, 1990

[54] PURIFICATION OF HIGH BOILING ALKYL SULFIDES

[75] Inventors: James E. Shaw; John S. Roberts, both of Bartlesville, Okla.

[73] Assignee: Phillips Petroleum Company, Bartlesville, Okla.

[21] Appl. No.: 280,337

[22] Filed: Dec. 6, 1988

[51] Int. Cl.$^5$ ................... B01D 3/34; C07C 319/26
[52] U.S. Cl. .......................................... 203/6; 203/29; 203/33; 203/36; 203/37; 203/38; 568/19; 568/38; 568/59; 568/60
[58] Field of Search ................... 203/6, 33, 36, 37, 38, 203/59, 29; 568/19, 59, 60, 38

[56] References Cited

U.S. PATENT DOCUMENTS

| | | | |
|---|---|---|---|
| 2,020,421 | 11/1935 | Lee | 568/60 |
| 2,594,311 | 4/1952 | Johnson et al. | 585/854 |
| 2,818,388 | 12/1957 | Sullivan et al. | 568/19 |
| 2,948,683 | 8/1960 | Sullivan et al. | 568/19 |
| 3,345,292 | 10/1967 | Neale et al. | 568/19 |
| 3,376,203 | 4/1968 | Lackey | 203/37 |
| 3,454,651 | 7/1969 | Warner et al. | 568/26 |
| 4,355,183 | 10/1982 | Nash et al. | 568/19 |
| 4,568,767 | 2/1986 | Dzierza et al. | 568/59 |

FOREIGN PATENT DOCUMENTS 1293199 2/1987 U.S.S.R. ................. 568/59

Primary Examiner—Wilbur Bascomb
Attorney, Agent, or Firm—Laney, Dougherty, Hessin & Beavers

[57] ABSTRACT

A process for preventing the substantial decomposition of an alkyl sulfide compound at high temperatures comprising combining a non-reactive basic compound with the alkyl sulfide compound prior to subjecting the resultant mixture to the high temperatures.

20 Claims, No Drawings

PURIFICATION OF HIGH BOILING ALKYL SULFIDES

BACKGROUND OF THE INVENTION

1. Field Of The Invention

The present invention relates generally to the purification of high boiling alkyl sulfide compounds, and more particularly, to preventing the decomposition of such alkyl sulfide compounds when subjected to high temperatures such as those encountered in a distillation process.

2. Description Of The Prior Art

High boiling alkyl sulfides are useful in various applications. For example, di-n-octyl sulfide is useful as an agent in the leaching of ores to recover precious metals, e.g., platinum.

The problem encountered in the production and purification of alkyl sulfides, particularly high boiling alkyl sulfides, is that they decompose when subjected to high temperatures, i.e., temperatures over about 100° C. Such decomposition prevents high purity alkyl sulfide products from being obtained in processes involving high temperatures, and causes that which is obtained to be discolored.

By the present invention processes for purifying high boiling alkyl sulfides whereby their decomposition is prevented are provided

SUMMARY OF THE INVENTION

In one aspect of the present invention, a process for substantially preventing the decomposition of a high boiling alkylsulfide compound when subjected to high temperatures is provided. In accordance with the process, a non-reactive basic compound is combined with the alkyl sulfide compound prior to subjecting the resulting mixture to high temperatures. The presence of the basic compound substantially prevents the decomposition of the alkyl sulfide compound.

In another aspect of the present invention, a process for purifying a high boiling alkyl sulfide compound in ad mixture with one or more impurity compounds without substantially decomposing the alkyl sulfide compound is provided. The process comprises combining an effective amount of a non-reactive basic compound with the mixture of alkyl sulfide compounds and impurity compounds, and then distilling the resulting mixture to obtain a high purity substantially colorless alkyl sulfide product.

It is, therefore, a general object of the present invention to provide a process for the purification of high boiling alkyl sulfides.

A further object of the present invention is the provision of a process for preventing the decomposition of one or more high boiling alkyl sulfide compounds when such compounds are subjected to high temperatures.

Another object of the present invention is the provision of a process for purifying high boiling alkyl sulfides in admixture with one or more impurity compounds without substantially decomposing the alkyl sulfides.

Other and further objects, features and advantages of the present invention will be readily apparent to those skilled in the art upon a reading of the description of preferred embodiments which follows.

DESCRIPTION OF PREFERRED EMBODIMENTS

High boiling alkyl sulfides are subject to substantial decomposition at high temperatures, i.e., temperatures above about 100° C. Such decomposition prevents the recovery of a high purity and colorless alkyl sulfide product in that the decomposition reduces the purity and imparts a yellow color to the product. The term "high boiling alkyl sulfide(s)" and the term "alkyl sulfide(s)" are 30 used herein to mean dialkyl sulfides containing eight or more carbon atoms. The two alkyl groups of the dialkyl sulfides can be the same or different and can be branched, unbranched, cyclic, or unsaturated. Examples of such high boiling alkyl sulfides are di-n-butyl sulfide, di-n-pentyl sulfide, di-n-hexyl sulfide, di-n-octyl sulfide, di-n-decyl sulfide, di-n-dodecyl sulfide, di-n-hexadecyl sulfide, di-cyclohexyl sulfide, di-(2-octyl) sulfide, n-decyl methyl sulfide, t-butyl n-dodecyl sulfide and allyl n-dodecyl sulfide.

An example of a circumstance where the disadvantages associated with the high temperature decomposition of high boiling alkyl sulfides is encountered involves di-n-octyl sulfide. That is, a process commercially utilized for producing n-octyl mercaptan comprises reacting 1-octene with an excess of hydrogen sulfide in the presence of ultraviolet light. The n-octyl mercaptan produced also reacts with 1-octene in the presence of ultraviolet light to produce a di-n-octyl sulfide byproduct. The various reactions can be represented as follows:

$$CH_3(CH_2)_5CH=CH_2 + H_2S \xrightarrow{UV\ light} CH_3(CH_2)_5CH_2CH_2SH$$

$$CH_3(CH_2)_5CH_2CH_2SH + CH_3(CH_2)_5CH=CH_2 \xrightarrow{UV\ light}$$

$$CH_3(CH_2)_5CH_2CH_2-S-CH_2CH_2(CH_2)_5CH_3$$

The byproduct di-n-octyl sulfide is typically comprised of about 72% by weight di-n-octyl sulfide with the remainder being comprised of lower boiling impurity compounds such as an isomeric sulfide (n-octyl, 2-octyl sulfide), n-octyl mercaptan and various other impurity compounds. In order to purify the di-n-octyl sulfide so that it can be commercially utilized, the byproduct mixture of di-n-octyl sulfide and impurity compounds can be subjected to fractional distillation. However, because in the distillation process the separated and purified di-n-octyl sulfide is subjected to high temperatures, a substantial portion of the di-n-octyl sulfide decomposes into di-n-octyl mercaptan and 1-and 2-octene. Such decomposition significantly reduces the purity of the di-n-octyl sulfide product obtained and causes the product to have a yellow color.

In order to prevent the decomposition of high boiling alkyl sulfide or a mixture of alkyl sulfides in accordance with the present invention, the alkyl sulfide or mixture is combined with an effective amount of one or more non-reactive basic compounds, and the resultant mixture is then subjected to high temperatures. The presence of the basic compound or compounds in admixture with the alkyl sulfide compound or compounds substantially prevents the decomposition of the alkyl sulfide compound or compounds at high temperatures.

Any of a variety of basic compounds which are non-reactive to alkyl sulfides and any impurity compounds in admixture therewith can be utilized. For example, non-reactive relatively high boiling organic amines and non-reactive alkali metal and alkaline earth metal hydroxides, carbonates, bicarbonates, oxides and sulfides can be used. The term "high boiling organic amines" is used herein to mean liquid organic amines which are not so volatile that they are completely vaporized at the high temperatures to which the alkyl sulfide in admixture therewith is subjected. Examples of such high boiling organic amines are 2,5-dimethoxyaniline, 1-aminonaphthalene and tetraethylenepentamine. Examples of suitable alkali metal hydroxides are sodium hydroxide, potassium hydroxide and lithium hydroxide. Examples of alkaline earth metal hydroxides are magnesium hydroxide, calcium hydroxide, barium hydroxide and strontium hydroxide. The same alkali metal and alkaline earth metal carbonates, bicarbonates, oxides and sulfides can also be utilized, e.g., sodium carbonate, calcium carbonate, sodium bicarbonate, sodium oxide, magnesium oxide and sodium sulfide. Of the foregoing basic compounds, alkali metal and alkaline earth metal hydroxides are preferred, with sodium hydroxide being the most preferred.

The basic compound used can be directly combined, either alone or in admixture with other non-reactive basic compounds, with one or more alkyl sulfide compounds in either liquid or solid form. Alternatively, the basic compound or compounds can be combined with the alkyl sulfide compound or compounds in an aqueous solution. When one or more alkali metal or alkaline earth metal hydroxides are utilized, they are preferably combined with the alkyl sulfide compound or compounds in the form of an aqueous solution, e.g., an aqueous solution containing about 50% by weight of the metal hydroxide or hydroxides.

The basic compound or compounds used are combined with the alkyl sulfide compound or compounds or with a mixture of one or more alkyl sulfide compounds and impurity compounds in an amount effective to prevent the decomposition of the alkyl sulfide compounds when subjected to high temperatures above about 100° C. The particular amount of basic compound which is effective can vary depending upon the particular alkyl sulfide compound or compounds involved, the presence of and type of impurity compounds in admixture therewith, the particular high temperatures to which the mixture is subjected and the particular basic compound or compounds utilized Generally, an amount of basic compound as low as about 0.001% by weight of the resulting mixture to as high as about 50% by weight of the resulting mixture can be effective. In the usual case when basic compounds such as alkali metal and alkaline earth metal hydroxides are utilized, an effective amount of basic compound is in the range of from about 0.01% to about 5% by weight of the alkyl sulfide and basic compounds in the resulting mixture which may or may not also include impurities. When sodium hydroxide is utilized, it is preferably combined with the alkyl sulfide compound or mixtures thereof in an amount in the range of from about 0.1% to about 1.0% by weight of the alkyl sulfide and basic compounds in the resulting mixture.

In carrying out the process of the present invention for purifying one or more high boiling alkyl sulfide compounds in admixture with one or more impurity compounds without substantially decomposing the alkyl sulfide compounds, an effective amount of one or more non-reactive basic compounds is first combined with the mixture of high boiling alkyl sulfide compounds and impurities in the amounts described above. The resulting mixture containing the basic compound or compounds is distilled or treated in a similar separation process involving high temperatures, to produce a high purity colorless alkyl sulfide product, i.e., a product which has not substantially decomposed. The distillation, fractional distillation or other similar technique used for separating impurities from the alkyl sulfide compound or compounds depends on the particular impurities present and their boiling points relative to the boiling points of the alkyl sulfides to be purified. Generally, the separation process will involve high temperatures within the range of from about 100° C to about 350° C, and more often in the range of from about 150° C to about 250° C.

In order to further illustrate the process of the present invention the following examples are given.

EXAMPLE 1

A byproduct mixture of di-n-octyl sulfide produced in the di-n-octyl mercaptan production process described above is subjected to fractional distillation to recover a purified di-n-octyl sulfide product. The composition of the di-n-octyl sulfide byproduct mixture is as follows:

| Component | Weight Percent |
|---|---|
| di-n-octyl sulfide | 71.6 |
| isomeric sulfide (n-octyl, 2-octyl sulfide) | 14.0 |
| n-octyl mercaptan | 5.0 |
| other lesser impurities | 9.4 |
| Total | 100.0% |

1,449 grams of the above byproduct mixture were subjected to fractional distillation in a column containing high efficiency stainless steel packing at a pressure of 2 torr. Initially, a reflux ratio of 2:1 was used to remove volatile impurities, i.e., mainly the di-n-octyl mercaptan; and then a 5:1 reflux ratio was used to remove the isomeric sulfide which had a boiling point slightly lower than the di-n-octyl sulfide. Mixed fractions of the isomeric sulfide and the di-n-octyl sulfide were obtained until the isomeric sulfide was completely removed. 49% by weight of the starting byproduct mixture was recovered as di-n-octyl sulfide having a 95.0% by weight purity. The final fractional distillation conditions were a reflux ratio of 1:20, a column head temperature in the range of from 162° C. to 169° C., a pot temperature in the range of from 203° C. to 212° C., and a column pressure of 2 torr. The recovered, di-n-octyl sulfide was yellow and contained 3.2% by weight di-n-octyl mercaptan and 0.4% by weight 1- and 2-octenes due to decomposition of di-n-octyl sulfide in the distillation pot.

EXAMPLE 2

1,327 grams of the di-n-octyl sulfide byproduct mixture described in Example 1 above were combined with 20 grams of a 50% by weight aqueous sodium hydroxide solution to form a mixture containing 0.75% by weight sodium hydroxide. The mixture was fractionally distilled in the same manner as described in Example 1. After the isomeric sulfide was removed, 46% by weight of the initial mixture was recovered as di-n-octyl sulfide of 98.6% by weight purity. The final distillation column conditions were a 1:20 reflux ratio, a column head temperature of from 166° C. to 167° C., a pot temperature of from 206° C. to 210° C., and a pressure of 2 torr. The di-n-octyl sulfide was colorless and contained only 0.4% n-octyl mercaptan and a trace (0.02%) of 1-and 2-octenes.

Thus, the present invention is well adapted to carry out the objects and attain the ends and advantages mentioned as well as those inherent therein. While numerous changes in process conditions and other variables can be made by those skilled in the art, such changes are encompassed within the spirit of this invention as defined by the appended claims.

What is claimed is:

1. A process for preventing the decomposition of a high boiling dialkyl sulfide compound containing 8 or more carbon atoms when subjected to high temperatures comprising:
   combining a basic compound which is non-reactive to said dialkyl sulfide compound in an amount effective to prevent said decomposition with said dialkyl sulfide compound; and
   subjecting the resultant mixture to said high temperature.

2. The process of claim 1 wherein said basic compound is selected from the group consisting of high boiling organic amines and alkali metal and alkaline earth metal hydroxides, carbonates, bicarbonates, oxides and sulfides.

3. The process of claim 1 wherein said basic compound is combined with said dialkyl sulfide compound in an amount in the range of from about 0.001% to about 50% by weight of the resulting mixture.

4. A process for preventing the decomposition of a high boiling alkyl sulfide compound when subjected to high temperatures comprising:
   combining a basic compound which is non-reactive to said alkyl sulfide selected from alkali metal and alkaline earth metal hydroxides in an amount effective to prevent said decomposition with said alkyl sulfide compound; and
   subjecting the resultant mixture to said high temperatures.

5. The process of claim 4 wherein said basic compound is combined with said alkyl sulfide compound in an amount in the range of from about 0.01% to about 5% by weight of the resulting mixture.

6. A process for purifying a high boiling alkyl sulfide compound in admixture with one or more impurity compounds without substantial decomposition of the alkyl sulfide compound comprising the steps of:
   combining a basic compound which is non-reactive to said alkyl sulfide compound and said impurity compounds in an amount effective to prevent said substantial decomposition of said alkyl sulfide compound with said mixture; and
   subjecting the resulting mixture to a high temperature separation process to obtain a high purity alkyl sulfide product.

7. The process of claim 6 wherein said basic compound is selected from the group consisting of boiling organic amines and alkali metal and alkaline earth metal hydroxides, carbonates, bicarbonates, oxides and sulfides.

8. The process of claim 6 wherein said basic compound is selected from an alkali metal and alkaline earth metal hydroxide.

9. The process of claim 8 wherein said basic compound is combined with said mixture of alkyl sulfide compound and impurity compounds in an amount in the range of from about 0.01% to about 5% by weight of the alkyl sulfide and basic compounds in the resulting mixture.

10. The process of claim 6 wherein said alkyl sulfide compound is di-n-octyl sulfide.

11. The process of claim 10 wherein said basic compound is sodium hydroxide, and is combined with said mixture of di-n-octyl sulfide and impurity compounds in an amount in the range of from about 0.1% to about 1.0% by weight of the di-n-octyl sulfide and sodium hydroxide in the resulting mixture.

12. The process of claim 11 wherein said sodium hydroxide is combined with said mixture of di-n-octyl sulfide and impurity compounds in the form of an aqueous solution of sodium hydroxide.

13. The process of claim 12 wherein said aqueous solution of sodium hydroxide contains sodium hydroxide in an amount of about 50% by weight of said solution.

14. In a distillation process for purifying di-n-octyl sulfide in admixture with one or more lower boiling impurities, the improvement whereby the purified di-n-octyl sulfide is prevented from substantial decomposition into n-octyl mercaptan and octene comprising:
   combining a basic compound which is non-reactive to said di-n-octyl sulfide and said impurities in an amount effective to prevent said substantial decomposition of said di-n-octyl with said mixture of di-n-octyl sulfide and lower boiling impurities; and then
   distilling said mixture to obtain a purified di-n-octyl sulfide bottom product.

15. The process of claim 14 wherein said basic compound is selected from the group consisting of non-reactive high boiling organic amines and non-reactive alkali metal and alkaline earth metal hydroxides, carbonates, bicarbonates, oxides and sulfides.

16. The process of claim 15 wherein said basic compound is combined with said mixture of di-n-octyl sulfide and lower boiling impurities in an amount in the range of from about 0.001% to about 50% by weight of the di-n-octyl sulfide and basic compound in the resulting mixture.

17. The process of claim 14 wherein said basic compound is an alkali metal or alkaline earth metal hydroxide.

18. The process of claim 17 wherein said basic compound is combined with said mixture of di-n-octyl sulfide and lower boiling impurities in an amount of about 0.01% to about 5% by weight of the di-n-octyl sulfide and basic compound in the resulting mixture.

19. The process of claim 14 wherein said basic compound is sodium hydroxide and is combined with said alkyl sulfide compound in an amount in the range of from about 0.1% to about 1.0% by weight of the di-n-octyl sulfide and basic compound in the resulting mixture.

20. The process of claim 19 wherein said sodium hydroxide is combined with said mixture of di-n-octyl sulfide and lower boiling impurities in the form of a 50% by weight aqueous solution of sodium hydroxide.

* * * * *

UNITED STATES PATENT AND TRADEMARK OFFICE
CERTIFICATE OF CORRECTION

PATENT NO. : 4,964,957
DATED : October 23, 1990
INVENTOR(S) : James E. Shaw and John S. Roberts It is certified that error appears in the above-identified patent and that said Letters Patent is hereby corrected as shown below:

Column 1, line 35, delete the word "alkylsulfide" and insert the words --alkyl sulfide--;

Column 2, line 11, delete the numeral "30";

Column 2, line 52, delete the word "di-n-octyl" and insert the word --n-octyl--;

Column 4, lines 21, 39 and 52, delete the word "di-n-octyl" and insert the word --n-octyl--;

Column 5, line 59, after the word "of" and before the word "boiling", insert the word --high--;

Column 6, lines 37 and 38, delete the word "non-reactive".

Signed and Sealed this

Twenty-eighth Day of April, 1992

Attest:

HARRY F. MANBECK, JR.

Attesting Officer     Commissioner of Patents and Trademarks